United States Patent [19]

Arnold

[11] Patent Number: 4,494,482

[45] Date of Patent: Jan. 22, 1985

[54] ANIMAL LITTER COMPOSITION

[75] Inventor: Nancy L. Arnold, Centerville, Ohio

[73] Assignee: The Procter & Gamble Company, Cincinnati, Ohio

[21] Appl. No.: 546,361

[22] Filed: Nov. 1, 1983

Related U.S. Application Data

[63] Continuation-in-part of Ser. No. 441,316, Nov. 12, 1982, abandoned.

[51] Int. Cl.$^3$ ............................................. A01K 1/015
[52] U.S. Cl. ...................................................... 119/1
[58] Field of Search ........................................... 119/1

[56] References Cited

U.S. PATENT DOCUMENTS

| | | | |
|---|---|---|---|
| 3,626,899 | 12/1971 | Spellman | 119/1 |
| 3,752,121 | 8/1973 | Brazzell | 119/1 |
| 3,762,875 | 10/1973 | Burmeister | 119/1 X |
| 3,765,371 | 10/1973 | Fisher | 119/1 |

*Primary Examiner*—Hugh R. Chamblee
*Attorney, Agent, or Firm*—J. D. Schaeffer; S. J. Goldstein; J. C. Rasser

[57] ABSTRACT

Solid absorbent materials, having adsorbed thereto from about 25 ppm to about 500 ppm of a halogenated aromatic hydrocarbon bacteriostat, when used as animal litter products, effectively prevent the development of urine odors.

Absorbent pads having adsorbed thereto from about 5000 ppm to about 30,000 ppm of the bacteriostat when used as liners in litter boxes likewise effectively control odor development.

19 Claims, No Drawings

ANIMAL LITTER COMPOSITION

REFERENCE TO RELATED APPLICATION

This is a continuation-in-part of application Ser. No. 441,316, filed Nov. 12, 1982, now abandoned.

TECHNICAL FIELD

This invention relates to an inexpensive absorbent animal litter product which is capable of preventing the development of unpleasant urine odors over an extended period of time.

The owners of household pets, in particular cats, perceive the development of urine odors in animal litter boxes as a significant problem. Attempts to alleviate this problem have ranged from the addition of a perfume to an absorbent animal litter product to processing alfalfa or another chlorophyll containing grass into an absorbent animal litter material. Both approaches are relatively expensive and have met with only limited success. Household pets tend to dislike the smell of such products and to avoid the use of the litter. Moreover, to the extent that these materials effectively mask or neutralize unpleasant odors, they are effective over only a limited period of time.

It is therefore an object of this invention to provide an absorbent animal litter material which prevents the development of unpleasant odors over an extended period of time. It is a further object of this invention to provide a method for preparing such an animal litter material.

BACKGROUND ART

Bacteriostats like 2,4,4'-trichloro-2'-hydroxydiphenyl ether are known deodorizers, and as such are used in deodorants, deodorant soaps, fabric sanitizers, and the like. Levels typically range from about 0.5% to about 5%. Furia et al., *Soap & Chemical Specialties*, January 1968, report that 20 ppm of the above compound on a diaper soiled with urine significantly reduced total microflora and total ammonia producing organisms in an overnight test. About 100 ppm reportedly reduced the viable cell counts by 90%. Although these data indicate that the compound is very effective, they do not suggest that it could be used in an animal litter product and be effective over a period of several weeks in eliminating ammonia and mercaptan odor.

Prior art attempts to deodorize cat litter include the addition of a perfume (see, e.g., U.S. Pat. No. 3,921,581, issued Nov. 25, 1975 to Brewer), and the addition of chlorophyll, mainly in the form of dried alfalfa to the litter (see, e.g., U.S. Pat. No. 3,923,005, issued Dec. 2, 1975 to Fry et al., assigned to The Clorox Company).

U.S. Pat. No. 4,129,094, issued Dec. 12, 1978 to Stockel, discloses the use of fly ash, bottom ash and/or boiler slag as cat litter materials. The composition of fly ash, as determined by the ASTM and cited in the patent, includes silicon dioxide, alumina, ferric oxide, calcium oxide, magnesium oxide, sodium oxide and potassium oxide.

SUMMARY OF THE INVENTION

This invention relates to a solid absorbent material useful as an animal litter, having adsorbed thereto from about 25 ppm to about 500 ppm of a broad spectrum bacteriostat. Suitable bacteriostats are the halogenated aromatic hydrocarbon bacteriostats. The bacteriostats may be used at such low levels that even the use of bacteriostats which are expensive and/or toxic does not cause any problems.

The animal litter material of this invention effectively prevents the development of unpleasant odors over an extended period of time. This invention further encompasses a method of making the subject animal litter product.

DETAILED DESCRIPTION OF THE INVENTION

As used herein, gas concentrations are volume in volume, unless indicated otherwise. The amounts of bacteriostat are expressed in weight of the bacteriostat by weight of the solid absorbent material. The bacteriostat is adsorbed to the solid adsorbent material by contacting the solid absorbent material with a solution, preferably an aqueous solution, of the bacteriostat. "Contacting" means wetting at least a significant portion of the surface area of the solid absorbent material with the bacteriostat solution, and thus includes impregnating, soaking, and spraying.

The unpleasant odors associated with the urine of household pets are perceived to be an important problem by the owners of such pets. It is therefore not surprising that the literature is replete with reports of attempts to alleviate this problem. Among the more notable examples are animal litter products to which perfume or chlorophyll has been added. The former may be in the form of encapsulated particles, the latter e.g. in the form of alfalfa pellets.

Although the odor problem has been addressed in various ways, little, if any, appears to be known about its nature. It is commonly assumed that ammonia is the major component of malodorous materials emanating from urine. This suggests that urease, the enzyme that converts urea to ammonia, would be responsible for the odor development. However, it has surprisingly been found that reducing ammonia levels to well below the olfactory detection threshold (ODT) does not eliminate the odor problem. It is being hypothesized that sulfides and mercaptans, which have olfactory detection thresholds in the ppb, or even ppt, range greatly contribute to the malodor generally associated with animal litter boxes. The ODT of ammonia is much higher than that: ca 50 ppm. See "Compilation of Odor and Taste Threshold Values Data", W. M. Stoke, ed., ASTM data series DS 48. In order to effectively prevent the development of malodors, an animal litter material must therefore be capable of eliminating sulfide and mercaptan odors. The capability of eliminating ammonia odor is of only secondary importance and may not be important at all, as it is unlikely that the amount of ammonia generated will exceed the ODT under normal conditions in the typical home.

It has now been found that when a normal absorbent animal litter material as is commercially available is contacted with a solution of a broad spectrum bacteriostat and is subsequently dried, an animal litter material is obtained which is capable of effectively preventing the development of unpleasant odors in animal litter boxes over a period of three weeks or more. It has further been discovered that effective odor prevention is obtained with very small amounts of the broad spectrum bacteriostat. This is important because many of these bacteriostats are toxic and/or expensive. One of the most important aspects of this invention is that expensive and toxic materials can be used at such low levels that an effective product is obtained without cost or toxicity being factors of any importance.

Any absorbent solid material suitable for use as an animal liter may be used in the present invention. Suitable examples include minerals, typically clay such as kaolinites, montmorillonites, or bentonites; fly ash as obtained from the burning of coal; but also absorbent fibrous webs like cellulosic webs or polymeric fibrous webs; pelletized absorbent materials (e.g. sawdust or polyurethane foam); and the like. Particle sizes typically range from about 0.1 inch to about 0.5 inch (from about 0.25 cm to about 1.3 cm). Other examples of suitable solid absorbent materials are disclosed in U.S. Pat. No. 3,921,581, issued Nov. 25, 1975 to Brewer, incorporated herein by reference.

Although any broad spectrum bacteriostat is suitable for use herein, including the alkyl monocarboxylic acids having from 3 to 9 carbon atoms, preferred bacteriostats are the halogenated aromatic hydrocarbons. By halogenated aromatic hydrocarbons as used herein is meant the halogenated phenols, halogenated diphenyls and halogenated bis-phenols. These bacteriostats are well known in the art, and generally used as disinfectants. Suitable examples are p-chloro-m-cresol; hexachlorophane; 2,4,4'-trichloro-2'-hydroxydiphenyl ether; trichlorocarbanilide (TCC); 2,4-dichloro-m-xylenol (DCMX); 3,4,5-tribromosalicylanilide (TBS) and 3,5,3',4'-tetrachlorosalicylanilide (TCS). Other examples of this family of bacteriostats are disclosed in Sykes, "Disinfection and Sterilization," 2nd edition (1965). Chapter 12, J. B. Lippincott, Philadelphia, publishers, the disclosures of which are incorporated herein by reference.

The preparation of the animal litter product of the present invention comprises the step of contacting a solid absorbent material with a solution of the bacteriostat. Most conveniently this solution is an aqueous solution, and water soluble bacteriostats are therefore preferred. Since small amounts of the bacteriostats are sufficient for obtaining an effective animal litter product, it is sufficient that the bacteriostat is only slightly soluble in water. A solubility of 0.5% is generally sufficient. Water-insoluble compounds may be dissolved in an organic solvent like acetone or ethanol, or in a mixture of water with, e.g., acetone, ethanol or 2-ethoxyethanol. TCC may be dissolved in an aqueous solution of soap, as is well known in the art of manufacturing deodorant soaps.

Animal litter products according to the present invention are prepared as follows. The calculated amount of bacteriostat is dissolved in an amount of solvent which is sufficient to completely saturate the solid absorbent material. The amount of solvent necessary will vary with the kind of absorbent material used and typically is in the range of from about 1 liter to about 5 liters per kg of solid absorbent material. The solid absorbent material is slurried with the bacteriostat solution. The slurry is then allowed to equilibrate for about 10 minutes. The slurry may be agitated by stirring or by vibrating which reduces the amount of time needed for equilibration. Subsequently, the solvent is drained off and the wet solid material is collected on e.g., a screen. The solid material is then dried at ambient conditions, or in an oven at a temperature of from about 50° C. to about 95° C. This procedure lends itself extremely well to a continuous process, whereby metered flows of solid absorbent material and bacteriostat solution are contacted with each other, the material is subsequently drained on a perforated conveyor belt and dried in an air-dry tunnel. The amount of solution may be such that it is just sufficient to saturate the absorbent material so that no draining step will be necessary. This insures quantitative deposition of the bacteriostat and eliminates the necessity of handling excess water.

The amount of bacteriostat needed for obtaining effective odor control varies with the potency of the compound. In general, 25 ppm by weight of the solid absorbent material is adequate, but preferably at least about 100 ppm is used. Amounts of over 500 ppm may be used, but no additional benefits result from the use of levels over 500 ppm. The bacteriostat level therefore should be below about 500 ppm, preferably below about 300 ppm.

A specific embodiment of the present invention is an absorbent pad of the type used in absorbent articles like disposable diapers, sanitary napkins, and the like, which has been treated with an appropriate amount of bacteriostat. If the pads are to be used as the sole absorbent material in the litter box, an appropriate amount of bacteriostat is from about 25 ppm to about 500 ppm by weight of the absorbent pad.

Very good results are obtained when the absorbent pad is used as a liner on the bottom of the litter box, and covered with a litter material of the type as is commercially available, e.g. absorbent clay particles. It has been discovered that the odor control benefits of the present invention are obtained even if only the pad has bacteriostat material adsorbed thereto. However, the amount of bacteriostat on the absorbent pad must be increased so as to account for the amount of untreated clay in conjunction with which the pad will be used.

For example, if a pad weighing 50 g is designed for use in conjunction with 2000 g of untreated clay, the pad must be treated with 4100 ppm of the bacteriostat material in order to obtain an overall bacteriostat level of 100 ppm by weight of the combined absorbent materials in the litter box. In general terms, if w is the weight of the pad, W is the weight of the untreated absorbent material to be used in conjunction with the pad, and b (in ppm) is the desired overall level of bacteriostat, the level of bacteriostat B (in ppm) with which the pad must be treated is given by $$B = [(w+W)/w] \times b$$

Typically, b ranges from about 25 ppm to about 500 ppm, w ranges from about 20 g to about 100 g, and W from about 400 g to about 3000 g, hence B ranges from about 125 ppm to about 75000 ppm.

A preferred embodiment of the present invention is a flexible absorbent structure comprising a mixture of hydrophilic fibers and discrete particles of a water-insoluble hydrogel, in a fiber/hydrogel ratio of from about 30:70 to about 98:2, said absorbent structure having a density of from about 0.15 to about 1 g/cm$^3$, and having absorbed thereto from about 5000 ppm to about 30,000 ppm of a halogenated aromatic hydrocarbon bacteriostat.

Preferably, the fiber/hydrogel ratio is from about 50:50 to about 95:5, more preferably from about 75:25 to about 90:10. Preferred densities are in the range of from about 0.15 to about 0.6 g/cm$^3$, more preferred are densities in the range of from about 0.25 to about 0.4 g/cm$^3$.

By "hydrogel" as used herein is meant an inorganic or organic compound capable of absorbing aqueous fluids and retaining them under moderate pressures. For good results, the hydrogels must be water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarsson et al., Aug. 26, 1975, the disclosures of which are incorporated herein by reference. Particularly preferred polymers for use herein are hydrolyzed acrylonitrile grafted starch, acrylic acid grafted starch, polyacrylates, and isobutylene maleic anhydride copolymers, or mixtures thereof.

Processes for preparing hydrogels are disclosed in U.S. Pat. No. 4,076,663, issued Feb. 28, 1978 to Fusayoshi Masuda et al.; in U.S. Pat. No. 4,286,082, issued Aug. 25, 1981 to Tsuno Tsubakimoto et al.; and further in U.S. Pat. Nos. 3,734,876, 3,661,815, 3,670,731, 3,664,343, 3,783,871, and Belgian Pat. No. 785,858; the disclosures of all of which are incorporated herein by reference.

As used herein "Particles" include particles of any shape, e.g. spherical or semi-spherical, cubic, rod-like, polyhedral, etc.; but also shapes having a large greatest dimension/smallest dimension ratio, like needles, flakes and fibers, are contemplated for use herein. By "particle size" as used herein is meant the weight average of the smallest dimension of the individual particles. Conglomerates of hydrogel particles may also be used, provided the weight average size of such conglomerates is within the limits set forth hereinbelow.

Although the absorbent structures of the present invention are expected to perform well with hydrogel particles having a particle size varying over a wide range, other considerations may preclude the use of very small or very large particles. For reasons of industrial hygiene, (weight) average particle size smaller than about 30 microns are less desirable. Particles having a smallest dimension larger than about 4 mm may cause a feeling of grittiness in the absorbent structure, which is undesirable from a consumer standpoint. Preferred for use herein are particles having an (weight) average particle size of from about 50 microns to about 1 mm.

The type of hydrophilic fibers is not critical for use in the present invention. Any type of hydrophilic fiber which is suitable for use in conventional absorbent products is also suitable for use in the absorbent structure of the present invention. Specific examples include cellulose fibers, rayon, polyester fibers. Other examples of suitable hydrophilic fibers are hydrophilized hydrophobic fibers, like surfactant-treated or silica-treated thermoplastic fibers. Also, fibers which do not provide webs of sufficient absorbent capacity to be useful in conventional absorbent structures, but which do not provide good wicking properties, are suitable for use in the absorbent structures of the present invention. This is so because, for the purposes of the present invention, wicking properties of the fibers are far more important than their absorbent capacity. For reasons of availability and cost, cellulose fibers, in particular wood pulp fibers, are preferred.

A specific embodiment of a liner for litter boxes comprises the flexible absorbent structure described hereinabove, placed between a water-impervious backsheet (e.g. polyethylene or polypropylene), and a liquid-pervious hydrophobic topsheet. Backsheet and topsheet materials are well known in the art of disposable diapers. Examples of such materials are disclosed in U.S. Pat. No. 3,952,765, issued Apr. 27, 1976 to Duncan; and in U.S. Pat. No. 3,860,003, issued Jan. 14, 1975 to Buell, the disclosures of which are incorporated herein by reference.

To protect the liner from being torn by cat's claws, it may be covered with or encased in a wire mesh screen, preferably a nylon screen. The mesh size should be such as to permit unrestricted pass through of fluid, and the wire diameter should be such as to resist tear by a cat. Nylon wire screens as are used in screen windows are particularly suitable for this purpose.

Since the pads are highly absorbent, the above described process for impregnating absorbent material with bacteriostat by soaking in an aqueous solution of the bacteriostat is not well suited for these pads. Instead, the bacteriostat may conveniently be applied to the pad by spraying the pad with a solution of the bacteriostat in a volatile organic solvent (e.g. ethanol).

It has been discovered that in certain instances fungi may develop in the litter box. It is therefore desirable to adsorb a fungicide onto the pad, in addition to the bacteriostat. It has been discovered that undecylenic acid at 2000 ppm level effectively controls the growth of fungi.

EXAMPLE I

Samples of a clay cat litter product (CAT'S PRIDE, from Oil-Dri Corporation of America, Chicago, Ill.) were treated with solutions of 2,4,4'-trichloro-2'-hydroxydiphenylether in ethanol by the batch method described above at the rate of 25 ml solution per 15 g of clay. The samples were stirred until the litter was thoroughly saturated with the entire solution. The wet material was then dried in an oven at 93° C. Samples containing 100 ppm and 500 ppm, respectively, of the bacteriostat were made. 15 g of the litter product were weighed into a container and treated with 15 ml of cat urine. (When catheterized cat urine was used *Proteus vulgaris* was added, as *Proteus vulgaris* is present in normal cat urine and not in catheterized cat urine). The container was closed and the head space above the litter material was analyzed for ammonia and sniffed for odor development by two independent panelists once every weekday after start of the test. A control test was run with untreated samples of CAT's PRIDE clay litter. The samples treated with the chlorinated hydroxydiphenylether did not develop an odor or a measurable amount of ammonia during a period of 35 days, whereas the control samples started to develop a very strong pungent odor and significant amounts of ammonia (200 ppm or more) after a period of 21 days.

Samples of clay litter product was treated with 2,4,5-trichlorophenol (50 ppm); dichlorophene (100 ppm); hexachlorophane (150 ppm), 2,2'-dihydorxy-3,5,3',5'-tetrachlorodiphenyl sulfide (200 ppm); TBS (250 ppm), TCS (25 ppm) and DCMX (300 ppm). The resulting products effectively prevent the development of malodors when used as an animal litter product.

By the same method, the following absorbent solid materials, having a bacteriostat adsorbed thereto, are prepared:

Bentonite clay +100 ppm 2,4,5-trichlorophenol; fly ash pellets (ca 1 cm particle size) +50 ppm dichlorophene; cellulose fiber web +300 ppm hexachlorophane;

sawdust pellets (ca 0.5 cm particle size) +TBS (200 ppm); and polyurethane foam pellets (ca 0.8 cm particle size) +25 ppm DCMX.

When used as animal litter products, these absorbent solid materials effectively prevent the development of urine odors.

EXAMPLE II

Southern soft wood slash pine fibers were dry mixed with an acrylic acid grafted starch hydrogel having a weight average particle size of about 250 microns ("Sanwet 1M 1000", from Sanyo Co., Ltd., Japan) in a fiber/hydrogel ratio of 80:20. The mixture was air-laid into webs having a basis weight of 390 g/m². The webs were compressed to a density of 0.3 g/cm³. The webs were cut into pads of 18 in.×13 in. (about 45×33 cm). The pads were enveloped in wet strength tissue paper having a basis weight of about 12 pounds per 3,000 square feet (about 20 g/m²), a dry tensile strength of about 700 g/inch in the machine direction and about 300 g/inch in the cross machine direction.

The enveloped pad was glued onto a 13 in.×17 in. (about 33 cm×43 cm) backsheet of embossed polyethylene film having a melt index of about 3 and a density of about 0.92 g/cm³. The ends of the backsheet were folded over the enveloped pad and attached with glue. Finally, the absorbent pad was covered with a topsheet of a hydrophobic but water and urine previous material. (Webline No. F 6211 from the Kendall Co. of Walpole, Mass., comprised of a non-woven rayon bonded with an acrylic latex). The pads, weighing about 70 g, were impregnated with Triclosan (2,4,4'-trichloro-2'-hydroxydiphenylether) by spraying an ethanol solution until a total of 1.15 g Triclosan was applied (about 16,400 ppm). The pads were air dried, then dried in an air circulating oven at 100° C.

To protect the pads from being torn by cat's claws, they were encased in nylon screen (of the type used in screen doors and windows) by wrapping the pads between two layers of screen and heat sealing the edges.

The pads were attached to the bottom of a disposable cardboard litter box, and covered with approximately 4.8 lbs. (about 2.2 kg) conventional clay litter.

The litter box was used for 21 days; no detectable odors developed.

Control litter boxes, identical to the above except that the pads had not been treated with Triclosan, were likewise used for 21 days. Used clay samples of both types of boxes were collected in closed jars, and the headspace of the jars was analyzed for ammonia by G.C.

It appeared that in clay samples from boxes containing a Triclosan treated pad, ammonia generation was greatly suppressed as compared to clay samples from boxes containing an untreated pad. This finding demonstrates that the bacteriostat in the pad effectively controls odor generation even in the untreated clay on top of the pad.

What is claimed is:

1. A solid absorbent material useful as an animal litter, having adsorbed thereto from about 25 ppm to about 500 ppm of a halogenated aromatic hydrocarbon bacteriostat.

2. The solid absorbent material of claim 1 wherein the halogenated aromatic hydrocarbon bacteriostat is water soluble.

3. The solid absorbent material of claim 1 wherein the amount of halogenated aromatic hydrocarbon bacteriostat is from about 100 ppm to about 300 ppm.

4. The solid absorbent material of claim 1 wherein the bacteriostat is selected from the group consisting of: p-chloro-m-cresol; hexachlorophane; 2,4,4'-trichloro-2'-hydroxydiphenyl ether; trichlorocarbanilide; 2,4-dichloro-m-xylenol; 3,4,5-tribromosalicylanilide; 3,5,3',4'-tetrachlorosalicylanilide; 3,5,3',5'-tetrachlorodiphenyl sulfide; and mixtures thereof.

5. The solid absorbent material of claim 1 wherein the bacteriostat is 2,4,4'-trichloro-2'-hydroxydiphenyl ether.

6. A flexible absorbent structure comprising a mixture of hydrophilic fibers and discrete particles of a water-insoluble hydrogel, in a fiber/hydrogel ratio of from about 30:70 to about 98:2, said absorbent structure having a density of from about 0.15 to about 1 g/cm³, and having absorbed thereto from about 5000 ppm to about 30,000 ppm of a halogenated aromatic hydrocarbon bacteriostat.

7. The flexible absorbent structure of claim 6 wherein the bacteriostat is selected from the group consisting of: p-chloro-m-cresol; hexachlorophane; 2,4,4'-trichloro-2'-hydroxydiphenyl ether; trichlorocarbanilide; 2,4-dichloro-m-xylenol; 3,4,5-tribromosalicylanilide; 3,5,3',4'-tetrachlorosalicylanilide; 3,5,3',5'-tetrachlorodiphenyl sulfide; and mixtures thereof.

8. The flexible absorbent structure according to claim 6, having a fiber/hydrogel ratio of from about 50:50 to about 95:5.

9. A flexible absorbent structure according to claim 6, having a density of from about 0.15 to about 0.6 g/cm³.

10. A flexible absorbent structure according to claim 6 wherein the hydrophilic fibers are wood pulp fibers.

11. A flexible absorbent structure according to claim 6 wherein the water-insoluble hydrogel is selected from the group consisting of hydrolized acrylonitrile grafted starch, acrylic acid grafted starch, polyacrylates, copolymers of isobutylene and maleic anhydride, and mixtures thereof.

12. A liner for use in a litter box comprising
(a) a liquid impervious backsheet;
(b) a hydrophobic topsheet; and
(c) an absorbent structure according to claim 6, said structure being placed between the backsheet and the topsheet.

13. The liner of claim 12 which is encased in nylon screen.

14. A method for preparing an animal litter product from a solid absorbent material, comprising the steps of:
(a) dissolving from about 25 ppm to about 500 ppm of a halogenated aromatic hydrocarbon bacteriostat in a suitable solvent;
(b) soaking the solid absorbent material in the bacteriostat solution; and
(c) drying the solid absorbent material.

15. The method as described in claim 14, wherein the solid absorbent material is a clay.

16. The method as described in claim 14, wherein the bacteriostat is water soluble and the solvent is water.

17. The method as described in claim 14, wherein the amount of bacteriostat is from about 100 ppm to about 300 ppm.

18. The method as described in claim 14, wherein the bacteriostat is selected from the group consisting of: p-chloro-m-cresol; hexachlorophane; 2,4,4'-trichloro-2'-hydroxydiphenyl ether; trichlorocarbanilide; 2,4-dichloro-m-xylenol; 3,4,5-tribromosalicylanilide; 3,5,3',4'-tetrachlorosalicylanilide; 3,5,3',5'-tetrachlorodiphenyl sulfide; and mixtures thereof.

19. The method as described in claim 14, wherein the bacteriostat is 2,4,4'-trichloro-2'-hydroxydiphenyl ether.

* * * * *